United States Patent [19]

Hookano

[11] Patent Number: 5,032,119
[45] Date of Patent: Jul. 16, 1991

[54] REUSABLE DIAPER

[76] Inventor: Robert W. Hookano, 3877 North 750 West, Kokomo, Ind. 46901

[21] Appl. No.: 493,385

[22] Filed: Mar. 14, 1990

[51] Int. Cl.[5] .................................................. A61F 13/15
[52] U.S. Cl. .................................. 604/385.1; 604/385.2
[58] Field of Search ................ 604/377, 385.1–386, 604/389, 391, 393, 394, 396, 397, 401, 402; 128/374–377

[56] References Cited

U.S. PATENT DOCUMENTS

| | | | |
|---|---|---|---|
| Re. 21,092 | 5/1939 | Lankenau | 604/399 |
| 2,905,176 | 9/1989 | Davidson | 604/378 |
| 3,418,337 | 12/1969 | Ruffo | 604/375 |
| 3,568,676 | 3/1971 | Guercio | 604/378 |
| 3,857,067 | 8/1989 | Wood et al. | 604/389 |
| 4,205,679 | 6/1980 | Repke et al. | 604/394 |
| 4,300,563 | 11/1981 | Brookfield | 604/377 |
| 4,336,803 | 6/1982 | Repke | 604/377 |
| 4,338,938 | 7/1982 | Seavitt | 604/385.2 |
| 4,402,690 | 9/1983 | Redfern | 604/385.2 |
| 4,413,996 | 11/1983 | Taylor | 604/382 |
| 4,661,102 | 4/1987 | Shikata et al. | 604/385.2 |
| 4,773,906 | 9/1988 | Krushel | 604/391 |
| 4,801,298 | 1/1989 | Sorenson et al. | 604/386 |
| 4,938,754 | 7/1990 | Mesek | 604/385.2 |

FOREIGN PATENT DOCUMENTS 2427795  2/1980  France .................................. 604/377

Primary Examiner—Randall L. Green
Assistant Examiner—K. Reichle
Attorney, Agent, or Firm—Terry M. Gernstein

[57] ABSTRACT

An reusable diaper is in the shape of a disposable diaper and includes an all cotton main body and an all-cotton liner fixed to the main body. The liner has cotton fill material therein and hook-and-loop fastening material is also mounted on the main body. Strips of elastic material are also mounted on the main body.

1 Claim, 2 Drawing Sheets

REUSABLE DIAPER

TECHNICAL FIELD OF THE INVENTION

The present invention relates to the general art of diapers, and to the particular field of reusable diapers.

BACKGROUND OF THE INVENTION

At one time or another, nearly every baby needs some form of diaper. These diapers become soiled and must be changed for a clean and dry diaper to avoid a risk of a rash or a disease. Changing a soiled diaper has generally been viewed as being an onerous task.

At one time, nearly all diapers were made of cloth due to the benefits associated with cloth. Such benefits include softness, comfort and aeration as well as other advantages. However, cloth diapers can cost as much as one dollar apiece, and thus each cloth diaper should be used several times before being discarded in order to justify such cost.

Heretofore, most cloth diapers were generally rectangular in peripheral shape and were somewhat awkward to put on a baby, especially if that baby were moving and squirming about. Furthermore, such cloth diapers tended to gap about the baby's legs, loosen in use and become unsightly even though they were only slightly soiled.

Thus, mainly for reasons of convenience, the cloth diaper was replaced by disposable diapers. A disposable diaper generally includes at least one layer of plastics-type material and one layer of moisture-absorbent material, as well as adhesive fastening elements.

Such diapers are simply disposed of when soiled, and thus avoid many of the problems associated with cloth diapers. Also, such disposable diapers are generally easier to change, even in public; whereas cloth diapers are not so convenient when viewed in this respect.

While having many convenient attributes, disposable diapers still have several drawbacks. For example, plastic and paper are not as comfortable to a baby as is cloth, especially cotton. Furthermore, disposable diapers are much more expensive than are cloth diapers. The quantity of cloth diapers purchasable for between one and two hundred dollars is generally sufficient to last completely through a baby's diaper years; whereas disposable diapers can cost upwards of twenty cents apiece, and may be wasted as the baby grows. The number of diapers used during a baby's diaper years may make twenty cents apiece a very large number.

Still further, while a disposable diaper is discarded and is completely useless after use, and is generally useless after a baby outgrows the diaper years, cloth diapers can be used for many other applications, including washing cars, dusting, packing and the like, and thus become even more economical with regard to disposable diapers when such additional uses are considered.

Still further, while a disposable diaper may be time saving by not requiring laundering, even including the cost of a diaper service, cloth diapers are much cheaper than disposable diapers.

However, by far the most important drawback to disposable diapers vis a vis cloth diapers is the non-degradable nature of the disposable diapers. Once used and discarded, the disposable diaper remains intact for years. Disposable diapers are around and are a problem long after the baby has outgrown the diapers. Many municipal trash disposal sites are in danger of being overrun by disposable diapers. Thus, disposable diapers may represent a threat the environment.

Therefore, there is a need for all cloth diaper which has the convenience, aesthetics and fit of a disposable diaper, yet will retain the advantages, cost-effectiveness and environmental neutrality of cloth diapers.

OBJECTS OF THE INVENTION

It is a main object of the present invention is to provide an all cloth diaper which has the convenience, aesthetics and fit of a disposable diaper.

It is another object of the present invention to provide an all cloth diaper which has the convenience, aesthetics and fit of a disposable diaper, yet will retain the advantages, cost-effectiveness and environmental neutrality of cloth diapers.

SUMMARY OF THE INVENTION

These, and other, objects are achieved by an all-cotton diaper which is shaped to fit comfortably and quickly onto a baby, yet will retain its shape and aesthetic appearance in use.

The diaper includes an all-cotton I-shaped main body on which an all-cotton I-shaped liner is mounted as well as elastic material and releasable attaching elements. The diaper is shaped to be expeditiously placed on the baby and easily closed in a snug manner. The elastic material ensures a snug in-use fit for the diaper.

The diaper thus realizes nearly all of the advantages of cloth diapers along with most of the advantages associated with disposable diapers while avoiding most of the drawbacks associated with each type of diaper.

BRIEF DESCRIPTION OF THE DRAWING FIGURES

DETAILED DESCRIPTION OF THE PREFERRED EMBODIMENT OF THE INVENTION

Figure 1:
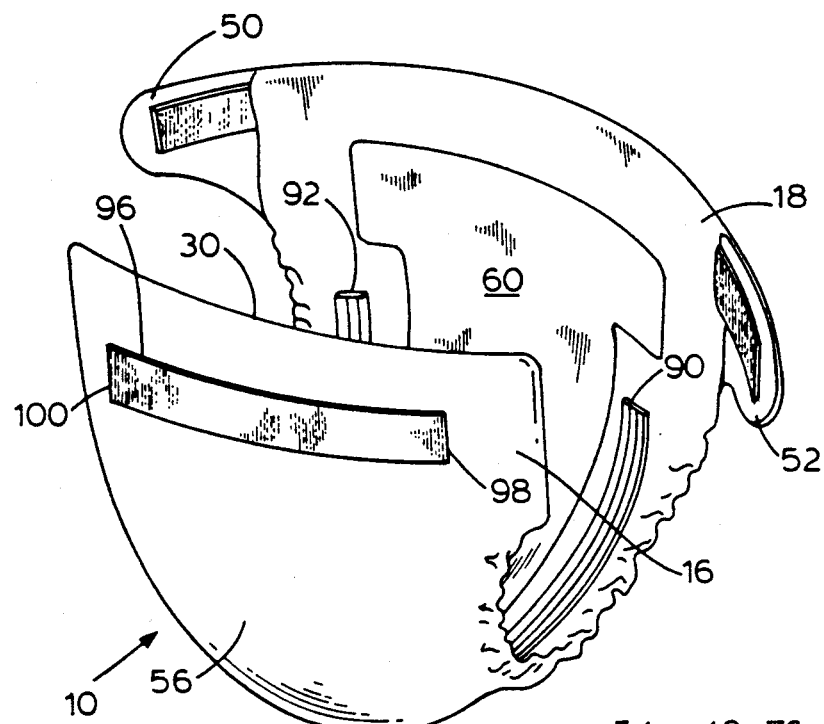
FIG. 1 is a perspective view of an all-cotton diaper embodying the present invention.
Figure 2:
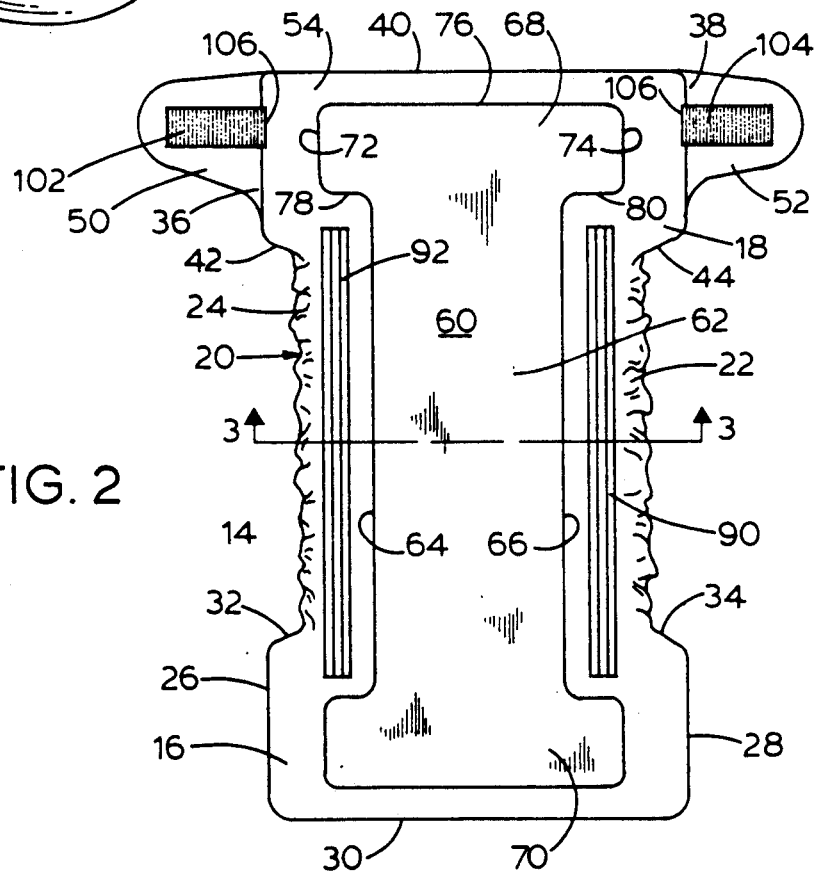
FIG. 2 is a top plan view of the diaper.

Shown in FIGS. 1 and 2 is an all-cotton diaper 10 which is adapted to be worn by a baby around the waist in the manner of a usual diaper. The diaper 10 is all cotton and thus achieves the advantages associated with cotton, yet is designed in such a manner as to be placed on a baby in the manner of a disposable diaper. It is the easy placement of the diaper onto the baby that has been one of the major advantages associated with disposable diapers vis a vis cloth diapers. The diaper 10 achieves this advantage with an all cotton diaper.

The diaper 10 includes a monolithic all-cotton main body 12 which has a peripheral shape similar to a block "I" with a central section 14 and first and second end sections 16 and 18, respectively. The central section 14 has side edges 20 and 22 which have gathering 24 thereon and has a width dimension measured between the two side edges.

The first end section 16 has side edges 26 and 28 and end edges 30, 32 and 34, with a width measured between the side edges 26 and 28 that is greater than the width of the central section. The end edges 32 and 34 intersect the central section side edges to define shoulders.

The second end section 18 has side edges 36 and 38 and end edges 40, 42 and 44, with a width measured between the side edges 36 and 38 that is essentially equal to the width of the first end section. The end edges 42 and 44 intersect the side edges of the central section to define shoulders.

Tabs 50 and 52 are attached to the side edges of the end section 18 and extend outwardly therefrom. The main body has an inner surface 54 which will be located adjacent to the baby when the diaper is in use on that baby, and an outer surface 56, and the main body has a longitudinal axis that extends between the ends 30 and 40.

Figure 4:
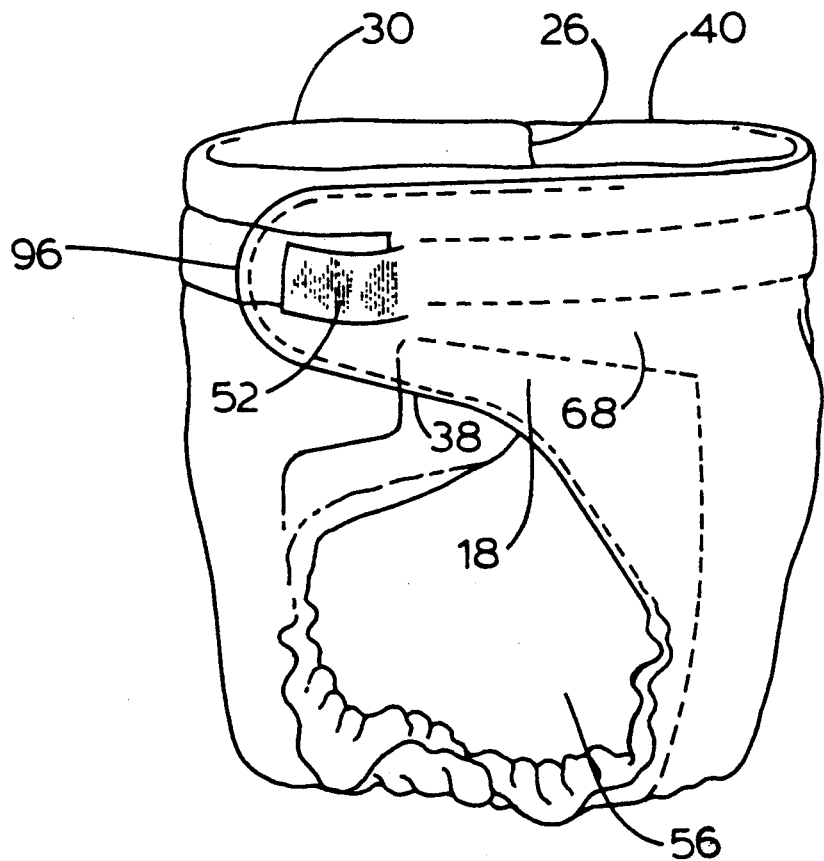
FIG. 4 is a perspective view of the diaper in a closed configuration.

The "I" shape of the main body will define leg openings, such as leg opening 56 shown in FIG. 4 when the diaper is closed. In use, the end section 16 will be located anteriorly of the baby and the end section 18 will be located posteriorly of the baby.

Figure 3:
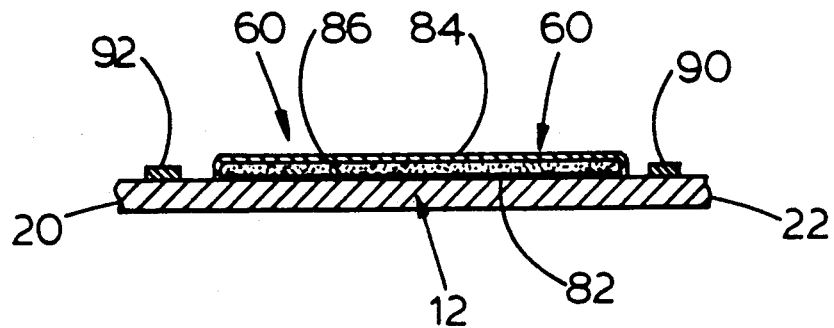
FIG. 3 is an elevational view taken along line 3—3 of FIG. 2.

As best shown in FIGS. 1, 2 and 3, the diaper includes an all-cotton liner 60 fixedly mounted on the main body inner surface 54. The liner is I-shaped and includes a central section 62 that overlies the main body central section and which includes side edges 64 and 66 which are spaced inwardly from the main body central section side edges 20 and 22 and which has a width as measured between the side edges 64 and 66 that is less than the width of the main body central section.

The liner also includes identical first and second end sections 68 and 70. Each of the liner end sections includes side edges, such as side edges 72 and 74 which are spaced apart by the width of the liner end section and which are spaced inwardly of the main body end section side edges, such as edges 36 and 38 so that the widths of the liner end sections are less than the widths of the main body end sections. The liner end sections also include end edges, such as end edges 76, 78 and 80 of end section 68, with the end edges 78 and 80 intersecting the liner side edges 64 and 66. The length dimension of the liner is measured between the end edges 76 and is less than the length of the main body.

The liner 60 includes an outer layer 82 that is fixedly mounted on the main body inner surface, and an inner layer 84 that is connected to the inner layer 82 along the liner edges but is spaced therefrom at other locations to form a closed pocket between such layers. A layer of cotton fill 86 is located between the liner inner and outer layers. The cotton fill layer is quite absorbent and thus serves to keep the baby dry.

Elastic material is located in strips 90 and 92 that are fixedly attached to the main body adjacent to the liner and the main body side edges, and which extend from between the liner and main body end edges associated with one end section of the liner to between the liner and main body end edges associated with the other main body end section. The elastic material serves to keep the diaper snugly engaged with the baby's legs when the diaper is in place on that baby. The elastic strips 90 and 92 preferably are formed of the same material as elastic strips commonly associated with underwear or like apparel.

The diaper 10 also includes releasable attaching means on the main body for releasably attaching one end section of the diaper main body to the other end section to form the diaper shown in FIG. 4. The preferred form of attaching means includes hook-and-loop type elements that are in strip form. Thus, the diaper 10 includes a fastening means first portion 96 of fastening means on the outside surface 56 of the main body and located adjacent to the end edge 30. The fastening means first portion 96 extends along the width dimension of the main body and is rectangular in shape to have end edges 98 and 100 located adjacent to the side edges of the main body end section 16.

Two fastening means strips 102 and 104 are fixedly mounted on the inner surface of the main body on the tabs 50 and 52 respectively. The strips 102 and 104 are rectangular in shape and have end edges 106 located closely adjacent to the end edges 36 and 38 of the main body end section 18.

As can be seen by comparing FIGS. 1 and 4, the strips 102 and 104 attach to the strip 96 adjacent to the ends of that strip 96, and can be moved with respect to those ends to loosen or tighten the diaper's fit on the baby. In this manner, the diaper can be sized and altered as the baby grows.

The diaper 10 is used in a manner that is similar to the use of a disposable diaper, except that the diaper 10 is all cotton and has the attributes of cotton and can be washed and reused.

However, the I-shape of the liner 60 will ensure that the baby remains dry and will not chafe next to the locations where the diaper is closed. The wings of the I, as defined by sides 72–80, will also space the attachment elements on the tabs 50, 52 away from the baby in a manner which increases comfort, and prevents wetness from leaking into and around the attachment elements and the attachment locations. The I-shape of the liner also permits the elastic strips 90 and 92 to be spaced from the baby's skin while extending to a close proximity of the attachment locations. This ensures a tight fit without chafing. Therefore, even if the elastic of the strips 90 and 92 loosen during wear, since the wings of the I-shaped liner extend adjacent to the strips, the diaper is not likely to leak. In the preferred embodiment shown in FIG. 2, the outside edges 72 and 74 of the liner are colinear with the outside edges of the elastic strips 90 and 92 so that the elastic strip is "protected" for its entire width by the liner. That is, the liner extends for more than the width of the strips and any loosening of the strips will be taken up by the presence of the liner. Thus, the I-shaped liner ensures comfort, yet does not vitiate the secure nature of the diaper's fit. The I shape of the liner also permits the elastic strips to be located in the most advantageous position to establish a secure fit about the baby's legs.

It is understood that while certain forms of the present invention have been illustrated and described herein, it is not to be limited to the specific forms or arrangements of parts described and shown.

I claim:

1. A resuable diaper comprising:
  A) a main body which is adapted to be placed on a baby, said main body being I-shaped and including
    (1) a central section having two side edges, a width measured between said side edges,
    (2) said central section having one end and a first end section at said central section one end, said first end section having side edges and a width measured between said first section side edges which is greater than said central section width, said first end section further including end edges which connect said first end section side edges to said central section side edges, respectively, said first end section having a top end edge spaced from said first end section end edges, said first end section having a length measured between said top end edge and said end edges, (3) said central section having another end and a second end section at said central secion another end, said second end section having side edges and a width measured between said second section side edges which is greater than said central section width, said second end section further including end edges which connect said second end section side edges to said central section side edges, respectively, said second end section having a top end edge spaced from said second end section end edges, said second end section width being equal to said first end section width, said second end section having a length measured between said second end section top end edge and said second end section end edges which is equal to said first end section length, (4) said main body having an overall length dimension measured between said end section top end edges, (5) a gatherable section of material along said main body central section side edges, respectively, (6) an inner surface which will be located next to the baby when the main body is in place on that baby, and (7) an outer surface;

B) an inner liner fixedly mounted on said main body inner surface, said inner liner being I-shaped so as to match the shape of said main body and including (1) a liner central section which overlies said main body central section, said liner central section having side edges, a width dimension measured between said liner central section side edges, said liner central section width being less than said main body central section width, (2) a liner first end section at one end of said liner central section, said liner first end section having parallel liner first end section side edges and a liner first end section width measured between said liner first section side edges which is greater than said liner central section width, said liner first end section further including co-linear liner first end section end edges which connect said liner first end section side edges to said liner central section side edges, respectively, said liner first end section having a liner top end edge spaced from said liner first end section end edges, said liner first end section overlying said main body first end section, said liner first end section having a length measured between said liner first end section top end edge and said liner first end section end edges, (3) a liner second end section at another end of said liner central section, said liner second end section having parallel liner second end sections side edges and a liner second end section width measured between said liner second section side edges which is greater than said liner central section width, said liner second end section further including co-linear liner second end section end edges which connect said liner second end section side edges to said liner central section side edges, respectively, said liner second end section having a liner second end section top end edge which is spaced from said liner second end section end edges, said liner second end section overlying said main body second end section, said liner second end section width being equal to the liner first end section width and said liner second end section side edges being collinear with the liner first end section side edges, said liner second end section top end edge being parallel to said liner first end section top end edge, said liner second end section end edges being parallel with said liner first end section end edges, said liner second end section having a length measured between said liner second end section top end edge and said liner second end section end edges, said liner second end section length being equal to said liner first end section length, (4) a liner inner layer fixed to said body inner surface, (5) a liner outer layer which will contact the baby when the main body is in place on the baby, (6) said liner inner layer being connected to said liner outer layer along said liner edges and being spaced from said liner outer layer at selected locations to define a liner pocket, and (7) said liner having a length dimension measured between said liner end section top end edges which is less than the length dimension of said main body;

C) said main body inner surface including first and second body areas between said main body central section side edges and said liner central section two side edges, respectively, first and second elongated strips of elastic material being mounted in said first and second body areas, respectively, each elongated strip of elastic material including a plurality of elongated areas, each strip having a first end located between said first end section end edges and said inner liner first end section end edges and a second end located between said second end section end edges and said inner liner second end section end edges and a length as measured between said strip first and second ends, all of said strip first ends being co-linear with each other and all of said strip second ends being co-linear with each other and all of said strip lengths being equal, each area having side edges connecting said strip first and second ends together, and said strip areas being positioned in side-by-side relationship with each other, said liner first and second end section side edges each being co-linear with an adjacent side edge of said strip side edges.

* * * * *